United States Patent [19]

Hsieh et al.

[11] Patent Number: 5,605,833
[45] Date of Patent: Feb. 25, 1997

[54] PROCESS FOR PREPARATION OF D-LACTIC ACID FROM D,L LACTIC ACID ESTER USING WHEAT GERM OR PANCREATIC LIPASE

[75] Inventors: Chun-Lung Hsieh; Jer-Yiing Houng, both of Hsinchu, Taiwan

[73] Assignee: Industrial Technology Research Institute, Hsinchu, Taiwan

[21] Appl. No.: 474,812

[22] Filed: Jun. 7, 1995

[51] Int. Cl.$^6$ .................................................. C12P 41/00
[52] U.S. Cl. .................................. 435/280; 435/139
[58] Field of Search ............................ 435/139, 280

[56] References Cited

U.S. PATENT DOCUMENTS 5,061,629  10/1991  Coffen et al. ............................ 435/280
5,248,610   9/1993  Miyazawa et al. ...................... 435/280

OTHER PUBLICATIONS

Parida S. et al., J. Org. Chem. 58: 3238–44 (1993).
Enzyme Nomenclature, Academic Press, Inc., pp. 270–273 (1984).
ATCC Catalogue of Filamentous Fungi pp. 365, 367 (1991).
Cambou B, Biotech Bioengin. vol. XXVI: 1449–54 (1984).

Primary Examiner—Irene Marx
Assistant Examiner—S. Saucier
Attorney, Agent, or Firm—W. Wayne Liauh

[57] ABSTRACT

A process is disclosed for the preparation of D-lactic acid from lactate racemic mixture. It comprises the steps of: (i) hydrolysis of an alkyl lactate racemic mixture in the presence of an esterase as a catalyst to hydrolyze L-alkyl lactate; (ii) separation of unhydrolyzed D-alkyl lactate with an organic solvent, such as n-hexane or a high alcohol; and (iii) chemical hydrolysis of the separated portion obtained from step (ii) with a base to obtain D-lactic acid. The esterase can be selected from the group consisting of pig pancreas lipase of the trade name Sigma L-3126, wheat germ lipase of the trade name Sigma L-3001, *Candida cyclindracea* lipase of the trade name Sigma L-1754, *Rhizopus lipase* of the trade name Serva 27930, *Mucor javanicus* lipase of the trade name Fluca 62304, *Aspergillus niger* lipase of the trade name Fluca 62301, *Rhizopus arrhizus* lipase of the trade name Boehringer Mannherin 414590, and *Candida cylindracea* cholesterol esterase of the trade name Boehringer Mannherin 396800.

3 Claims, No Drawings

PROCESS FOR PREPARATION OF D-LACTIC ACID FROM D,L LACTIC ACID ESTER USING WHEAT GERM OR PANCREATIC LIPASE

FIELD OF THE INVENTION

The present invention is directed to a process for the preparation of D-lactic acid comprising the steps of:
(i) hydrolysis of an alkyl lactate racemic mixture to hydrolyze L-alkyl lactate;
(ii) separation of unhydrolyzed D-alkyl lactate with an organic solvent; and
(iii) hydrolysis of the separated portion obtained from step (ii) with a base to produce D-lactic acid.

BACKGROUND OF DISCLOSURE

Lactic acid has a molecular structure $CH_3CH(OH)COOH$. It is the simplest optically active compound having D-and L-optical isomers as enantiomer.

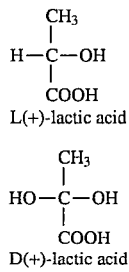

The two compounds differ only in optical activity while their chemical properties are completely identical. Lactic acid exists in nature as L-form. Microbial fermentation. produces only L-lactic acid. The production of D-lactic acid is very difficult. Since the preparation of some optically active pharmaceuticals needs D-lactic acid as a starting material which cannot be substituted by L-lactic acid, the preparation of D-lactic acid is very important.

Conventional processes for the preparation of D-lactic acid in laboratories include the followings:

(i) J. Indus. Microbial. 11:23–28, 1992 (Demirci) discloses a process for the preparation of D-lactic acid by screening a lactic acid producing strain from mutant mutant microorganisms and using the strain to produce lactic acid. The growth rate and the efficiency of producing D-lactic acid of the obtained strain are both relatively low.

(ii) D-and L-lactic acids are chemically synthesized. D-lactic acid is then separated from the D-and L-lactic acids by chemical resolution. The disadvantages of the process are that the efficiency is low and the separation steps are complicated.

(iii) The process disclosed in J. Biol. Chem. 243: 428–434, 1968 (Goldman) comprises converting the halogen group on the $C_2$ of the organic acid to —OH group with halidohydrolase while changing the stereo structure of the compounds at the same time. In the process, L-2-chloropropionic acid is converted to D-lactic acid. The reaction equation is as follows:

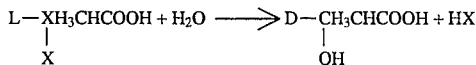

However, since fluoroacetic acid is necessary for the induction of bacterial production of halidohydrolase and fluoroacetic acid is highly toxic, bacteria grow very slowly. Hence, the yield of the production of halidohydrolase is low. It is hardly industrially applicable.

(iv) Appl. Biochem. Biotech. 22: 169–179, 1989 (Simon) discloses the reduction of pyruvic acid with D-lactate dehydrogenase to D-lactic acid. The process produces D-lactic acid based on the characteristic of D-lactate dehydrogenase in converting pyruvic acid to D-lactic acid. Nicotinamide adenine dinucleotide reduced form (NADH) is required in the system as a coenzyme of the reaction. Since the efficiency of the production of D-lactic acid is low and the coenzyme and D-lactate dehydrogenase are expensive and exhausted gradually during the reactions, the process is hardly industrially applicable.

(v) J. Am. Chem. Soc. 114: 893–897, 1992 (Biade) discloses a process for direct conversion of L-lactic acid to D-lactic acid. The process involves electrochemical reactions and enzymatic reactions to convert L-lactic acid directly to D-lactic acid. The process comprises adding L-lactate dehydrogenase, nicotinamide adenine dinucleotide (NAD) and L-lactic acid to an electrochemical reaction system. In the system, L-lactic acid is oxidized to pyruvic acid with L-lactate dehydrogenase. pyruvic acid is reduced to D-and L-lactic acid at the cathode. Since only L-lactate dehydrogenase is present in the system, L-lactic acid produced through electrochemical reduction will be further oxidizes to pyruvic acid while D-lactic acid remains in the system. At the anode of the system, reduced nicotinamide adenine dinucleotide reduced form is oxidized to oxidized nicotinamide adenine dinucleotide which further serves as a coenzyme of L-lactate dehydrogenase. The process is costly because of the consumption of the expensive L-lactate dehydrogenase and coenzyme. The low reaction efficiency at the electrochemical cathode and anode is another disadvantage of the process. Furthermore, since the amplification of the electrode plate is difficult, the process is hardly industrially applicable.

DETAILED DESCRIPTION OF THE INVENTION

The process for preparing D-lactic acid of the present invention comprises hydrolyzing a racemic mixture of alkyl lactate in the presence of an esterase at a pH in the range of 4 to 10, preferably in the range of 6 to 9, at a temperature in the range of 0° to 50° C., preferably 10° to 40° C., to hydrolyze L-alkyl lactate. The alkyl lactate used in the process of the present invention has the following general formula:

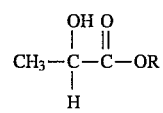

wherein R is $C_2$–$C_{16}$alkyl. The sources of the esterase suitable for the process of the present invention include lipase and cholesterol esterase. The hydrolysis rates of lipase and cholesterol esterase on L-and D-alkyl lactate are different. The unhydrolyzed D-alkyl lactate is separated by using organic solvents such as n-hexane, other water-immiscible organic solvents and alcohols. The separated portion is hydrolyzed with bases such as sodium hydroxide, potassium hydroxide and organic bases to produce D-lactic acid.

Lipase suitable for the present invention are isolated from the following organisms: plant sources such as wheat malt, animal sources such as pig, goat or calf pancreas, and microorganisms such as *Aspergillus niger, Rhizopus sp., Rhizopus arrhizus, Mucor javanicus* and *Candida cylindracea. Candida lipolytica, Chromobacterium viscosum, Penicillium rogurforti, Rhizopus delemar, Rhizopas niveus*. Cholesterol esterase refers to those separated from *Candida cylindracea*.

Lipase is an enzyme known for synthesis and hydrolysis of lipid. It has been recently found that lipase has different reaction rates on the two enantiomer of specific optically active compounds in hydrolysis, esterification or transesterification. Therefore, it is possible to produce pure optically active compounds by dynamic hydrolysis or esterification. Because of the variety of lipid hydrolysis and the big difference between compounds in characteristics, there is no rule to predict which lipase is suitable for optically resolving what enantiomer. Therefore, it is a particular technique to produce compounds through dynamic hydrolysis or esterification with lipase.

(1) Esterification of specific racemic isomers with lipase:

Lipase separated from pig pancreas (pig pancreas lipase, PPL) has faster esterification rate on the (−) form optically active isomer than the (+) form in a mixture of epoxy alcohol enantiomer. Therefore, two compounds, (−) form optically active ester and (+) form optically active alcohol, are obtained in the reaction and (+) form optically active epoxy alcohol of high purity can be produced. In the esterification of (+)-methyl-α-hydroxyphenylacetate and ethenylacetic acid, lipase separated from *Pseudomonas sp.* more selectively reacts on S-form optical isomer than R-form Methyl-R-α-hydroxyphenylacetate and methyl-S-α-acetoxyphenylacetate are obtained.

Lipase isolated from *Candida cylindracea* esterifies (±)-2-halopropionic acid, more selectively on (+)-2-halopropionic acid structure. Therefore, (+)-R-2-halopropionate and (−)-S-2-halopropionic acid of high purity are obtained.

(2) Hydrolysis of Racemic Mixtures with Lipase

Lipase isolated from *Pseudomonas fluorescens* hydrolyzes esters of (2RS,3E)-4-fluoro-3-beten-2-ol with higher hydrolysis rate on R-form. After separation and purification on column, optically active (2R, 3E)-4-fluoro-3-buten-2-ol of high purity is obtained.

Lipase isolated from *Candida cylindracea* hydrolyzes selectively on the (S)-form in (R,S)-2-methylphenylacetate and (S)-2-methylphenylacetic acid of high optical purity is obtained.

Lipase isolated from *Pseudomonas sp.* has higher hydrolysis capacity on R-form optical isomer in (R,S)-3-chloracetoxy-1-p-toluenesulfonyloxybutane and hence (R)-3-hydroxy-1-p-toluenesulfonyloxybutane and S-3-chloroacetoxy-1-p-toluenesulfonyloxybutane are obtained.

(3) Transesterification of specific esters with lipase:

Lipase isolated from pig pancreas (porcine pancreatic lipase) has higher transesterification rate between (S)-form in 2,2,2-trichloroethyl-(R,S)-3,4-epoxybutanoate and polyethylene glycols. (S)-polyethylene glycol epoxybutanoate and (R)-trichloroethyl epoxybutanoate of high optical purity are obtained.

The present invention is based on the discovery that specific esterases have different hydrolysis rates on L-and D-alkyl lactates. L-alkyl lactate is hydrolyzed and D-alkyl lactate remains, followed by separation of D-alkyl lactate from the reaction mixtures and hydrolysis of said D-alkyl lactate with a base to produce D-lactic acid. The present process uses esterases and alkyl lactates of low cost as starting materials and D-lactic acid of high purity is obtained. The present invention can be used to produce not only D-lactic acid but also D-alkyl lactate.

The following examples are illustrated to further describe the present invention but not limit the scope of the present invention.

EXAMPLE 1

14.22 mg lactic acid ethyl ester and 50 mg cholesterol esterase (produced by *Candida cylindracea* available from Boehringeer Mannherin Corporation, Product serial number 396800) were added to 1 ml phosphate buffer, pH 7.0 and stirred vigorously at 30° C. for 1.5 hours. 1 ml n-hexane was added. After centrifugation, 0.45 ml 2N sodium hydroxide was added to the supernatant and stirred vigorously at 30° C. for 16 hours to chemically hydrolyze the ethyl lactate which is not hydrolyzed by cholesterol esterase to lactic acid. The lactic acid obtained after hydrolysis was analyzed. The content of D-lactic acid and L-lactic acid in solution is respectively 96.88% and 3.12%. The optical purity (e.e %) of D-lactic acid is 93.76% and the enzymatic hydrolysis level is 53.1%.

e.e % of L-lactic acid used herein =

$$\left( \frac{\substack{\text{L-lactic acid concentration in the solution} - \\ \text{D-lactic acid concentration in the solution}}}{\substack{\text{L-lactic acid and D-lactic acid} \\ \text{total concentration in the solution}}} \right) \times 100\%$$

e.e % of D-lactic acid used herein =

$$\left( \frac{\substack{\text{D-lactic acid concentration in the solution} - \\ \text{L-lactic acid concentration in the solution}}}{\substack{\text{D-lactic acid and L-lactic acid} \\ \text{total concentration in the solution}}} \right) \times 100\%$$

EXAMPLE 2

14.3 mg lactic acid ethylester and 50 mg the enzyme used in Example 1 were added to 1 ml phosphate buffer, pH 7.0 and stirred vigorously at 30° C. for 2 hours. 1 ml n-hexane was added. After centrifugation, 0.45 ml 2N sodium hydroxide was added to the supernatant and stirred vigorously at 30° C. for 16 hours to chemically hydrolyze the ethyl lactate which is not hydrolyzed by cholesterol esterase to lactic acid. The lactic acid obtained after hydrolysis was analyzed. The content of D-lactic acid and L-lactic acid in solution is respectively 96.55% and 0.45%. The optical purity (e.e %) of D-lactic acid is 99.11% and the enzymatic hydrolysis level is 70.25%.

EXAMPLE 3

17.7 mg lactic acid n-butyl ester and 50 mg the enzyme used in Example 1 were added to 1 ml phosphate buffer, pH 7.0 and stirred vigorously at 37° C. for 1 hour. 1 ml n-hexane was added. After centrifugation, 0.45 ml 2N sodium hydroxide was added to the supernatant and stirred vigorously at 30° C. for 16 hours. The lactic acid obtained after sodium hydroxide hydrolysis was analyzed. The content of D-lactic acid and L-lactic acid in solution is respectively 98.99% and 1.01%. The optical purity (e.e %) of D-lactic acid is 97.99% and the enzymatic hydrolysis level is 52.66%.

EXAMPLE 4

20.0 mg lactic acid hexadecyl ester dissolved in 5 µl n-hexane and 50 mg the enzyme used in Example 1 were added to 1 ml phosphate buffer, pH 7.0 and stirred vigorously at 37° C. for 1.5 hours. 1 ml n-hexane was added. After centrifugation, 0.45 ml 2N sodium hydroxide was added to the supernatant and stirred vigorously at 30° C. for 16 hours. The lactic acid obtained after hydrolysis with sodium hydroxide was analyzed. The content of D-lactic acid and L-lactic acid in solution is respectively 97.61% and 2.39%. The optical purity (e.e %) of D-lactic acid is 95.22% and the enzymatic hydrolysis level is 90.88%.

EXAMPLE 5

17.7 mg lactic acid n-butyl ester and 80 mg lipase isolated from wheat germ (wheat germ lipase available from Sigma Corporation, Pharmaceutical Product Serial Number L-3001) were added to 1 ml trihydroxyaminomethane buffer, pH 9.0 and stirred vigorously at 25° C. for 3 hours. 1 ml n-hexane was added. After centrifugation, 0.45 ml 2N sodium hydroxide was added to the supernatant and stirred vigorously at 30° C. for 16 hours. The lactic acid obtained after hydrolysis with sodium hydroxide was analyzed. The content of D-lactic acid and L-lactic acid in solution is respectively 99.77% and 0.03%. The optical purity (e.e %) of D-lactic acid is 99.54% and the enzymatic hydrolysis level is 69.5%.

EXAMPLE 6

16.0 mg lactic acid n-propyl ester and 80 mg the enzyme used in Example 5 were added to 1 ml trihydroxyaminomethane buffer, pH 8.0 and stirred vigorously at 25° C. for 4 hours. 1 ml n-hexane was added. After centrifugation, 0.45 ml 2N sodium hydroxide was added to the supernatant and stirred vigorously at 30° C. for 16 hours. The lactic acid obtained after hydrolysis with sodium hydroxide was analyzed. The content of D-lactic acid and L-lactic acid in solution is respectively 83.53% and 16.47%. The optical purity (e.e %) of D-lactic acid is,67.06% and the enzymatic hydrolysis level is 88.01%.

EXAMPLE 7

19.4 mg lactic acid isoamyl ester and 80 mg the enzyme used in Example 5 were added to 1 ml phosphate buffer, pH 8.0 and stirred vigorously at 37° C. for 2 hours. 1 ml n-hexane was added. After centrifugation, 0.45 ml 2N sodium hydroxide was added to the supernatant and stirred vigorously at 30° C. for 16 hours. The lactic acid obtained after hydrolysis with sodium hydroxide was analyzed. The content of D-lactic acid and L-lactic acid in solution is respectively 99.5% and 0.5%. The optical purity (e.e %) of D-lactic acid is 98.99% and the enzymatic hydrolysis level is 67.5%.

EXAMPLE 8

20.85 mg lactic acid trans-2-hexenyl ester and 50 mg the enzyme used in Example 1 were added to 1 ml phosphate buffer, pH 7.0 and stirred vigorously at 30° C. for 1.5 hours. 1 ml n-hexane was added. After centrifugation, 0.45 ml 2N sodium hydroxide was added to the supernatant and stirred vigorously at 30° C. for 16 hours. The lactic acid obtained after hydrolysis with sodium hydroxide was analyzed. The content of D-lactic acid and L-lactic acid in solution is respectively 94.77% and 5.23%. The optical purity (e.e %) of D-lactic acid is 89.54% and the enzymatic hydrolysis level is 91.12%.

EXAMPLE 9

20.85 mg lactic acid trans-2-hexenyl ester and 80 mg the enzyme used in Example 5 were added to 1 ml phosphate buffer, pH 7.0 and stirred vigorously at 30° C. for 3 hours. 1 ml n-hexane was added. After centrifugation, 0.45 ml 2N sodium hydroxide was added to the supernatant and stirred vigorously at 30° C. for 16 hours. The lactic acid obtained after hydrolysis with sodium hydroxide was analyzed. The content of D-lactic acid and L-lactic acid in solution is respectively 90.96 and 9.04%. The optical purity (e.e %) of D-lactic acid is 81.92% and the enzymatic hydrolysis level is 83.6%.

EXAMPLE 10

20 mg lactic acid hexadecyl ester dissolved in 5 µl n-hexane and 80 mg lipase abstracted from *Candida cylindracea* (*Candida cylindracea* lipase available from Sigma Corporation, Product Serial Number L-1754) were added to 1 ml phosphate buffer, pH 7.0 and stirred vigorously at 30° C. for 4 hours. 1 ml n-hexane was added. After centrifugation, 0.45 ml 2N sodium hydroxide was added to the supernatant and stirred vigorously at 30° C. for 16 hours. The lactic acid obtained after hydrolysis with sodium hydroxide was analyzed. The content of D-lactic acid and L-lactic acid in solution is respectively 96.55% and 3.45%. The optical purity (e.e %) of D-lactic acid is 93.1% and the enzymatic hydrolysis level is 80.8%.

EXAMPLE 11

17.7 mg lactic acid n-butyl ester and 100 mg lipase purified from pig pancreas (porcine pancreas lipase available from Sigma Corporation, Pharmaceutical Product Serial Number L-3126) were added to 1 ml phosphate buffer, pH 7.0 and stirred vigorously at 37° C. for 2 hours. 1 ml n-hexane was added. After centrifugation, 0.45 ml 2N sodium hydroxide was added to the supernatant and stirred vigorously at 30° C. for 16 hours. The lactic acid obtained after hydrolysis with sodium hydroxide was analyzed. The content of D-lactic acid and L-lactic acid in solution is respectively 94.21% and 5.79%. The optical purity (e.e %) of D-lactic acid is 88.42% and the enzymatic hydrolysis level is 92.66%.

EXAMPLE 12

17.7 mg lactic acid n-butyl ester and 100 mg lipase purified from *Rhizopus sp.* (*Rhizopus sp.* lipase available from Serva Corporation, Product Serial Number 27930) were added to 1 ml phosphate buffer, pH 7.0 and stirred vigorously at 37° C. for 1 hour. 1 ml n-hexane was added. After centrifugation, 0.45 ml 2N sodium hydroxide was added to the supernatant and stirred vigorously at 30° C. for 16 hours. The lactic acid obtained after hydrolysis with sodium hydroxide was analyzed. The content of D-lactic acid and L-lactic acid in solution is respectively 98.78% and 1.22%. The optical purity (e.e %) of D-lactic acid is 97.56% and the enzymatic hydrolysis level is 93.72%.

EXAMPLE 13

17.7 mg lactic acid n-butyl ester and 100 mg lipase purified from *Mucor javanicus* (*Mucor javanicus* lipase available from Fluca Corporation, Product Serial Number 62304) were added to 1 ml phosphate buffer, pH 7.0 and stirred vigorously at 37° C. for 4 hours. 1 ml n-hexane was added. After centrifugation, 0.45 ml 2N sodium hydroxide was added to the supernatant and stirred vigorously at 30° C. for 16 hours. The lactic acid obtained after hydrolysis with sodium hydroxide was analyzed. The content of D-lactic acid and L-lactic acid in solution is respectively 91.3% and 8.7%. The optical purity (e.e %) of D-lactic acid is 82.6% and the enzymatic hydrolysis level is 88.13%.

EXAMPLE 14

17.7 mg lactic acid n-butyl ester and 100 mg lipase purified from *Aspergillus niger* (*Aspergillus niger* lipase available from Fluca Corporation, Product Serial Number 62301) were added to 1 ml phosphate buffer, pH 7.0 and stirred vigorously at 37° C. for 4 hours. 1 ml n-hexane was added. After centrifugation, 0.45 ml 2N sodium hydroxide was added to the supernatant and stirred vigorously at 30° C. for 16 hours. The lactic acid obtained after hydrolysis with sodium hydroxide was analyzed. The content of D-lactic acid and L-lactic acid in solution is respectively 87.5% and 12.49%. The optical purity (e.e %) of D-lactic acid is 75.2% and the enzymatic hydrolysis level is 87.5%.

EXAMPLE 15

17.7 mg lactic acid n-butyl ester and 100 mg lipase purified from *Rhizopus arrhizus* (*Rhizopus arrhizus* lipase available from Boehinger Mannherin Corporation, Product Serial Number 414590) were added to 1 ml phosphate buffer, pH 7.0 and stirred vigorously at 30° C. for 1 hour. 1 ml n-hexane was added. After centrifugation, 0.45 ml 2N sodium hydroxide was added to the supernatant and stirred vigorously at 30° C. for 16 hours. The lactic acid obtained after hydrolysis with sodium hydroxide was analyzed. The content of D-lactic acid and L-lactic acid in solution is respectively 80.02% and 19.98%. The optical purity (e.e %) of D-lactic acid is 60.04% and the enzymatic hydrolysis level is 90.77%.

We claim:

1. A process for the preparation of D-lactic acid comprising the steps of:

(a) hydrolyzing L-lactic acid alkyl ester from a racemic mixture of DL-lactic acid alkyl ester with a lipase obtained from wheat germ or pancreas as a catalyst;

(b) separating the unhydrolyzed D-lactic acid alkyl ester by extraction with an organic solvent; and hydrolyzing the D-lactic acid alkyl ester with a base to obtain D-lactic acid.

2. The process for the preparation of D-lactic acid according to claim 1 wherein the lipase is wheat germ lipase from Sigma L-3001.

3. The process for the preparation of D-lactic acid according to claim 1 wherein the lipase is pig pancreatic lipase from Sigma L-3126.

* * * * *